United States Patent [19]

Berger et al.

[11] Patent Number: 4,894,603
[45] Date of Patent: Jan. 16, 1990

[54] METHOD AND APPARATUS FOR ANALYSIS OF GAS BY MEANS OF ABSORPTION FREQUENCY REGULATION

[75] Inventors: Lutz Berger, Eggenstein; Heimo Breton, Oberuldingen; Helmut Giraud, Stutensee; Gunther Krieg, Karlsruhe; Horst Günther, Eggenstein-Leopoldshafen; Gerhard Schmitt, Karlsruhe, all of Fed. Rep. of Germany

[73] Assignee: Kernforschungszentrum Karlsruhe GmbH, Karlsruhe, Fed. Rep. of Germany

[21] Appl. No.: 71,657

[22] Filed: Jul. 9, 1987

[30] Foreign Application Priority Data

Jul. 9, 1986 [DE] Fed. Rep. of Germany ....... 3622957

[51] Int. Cl.$^4$ ............................................. G01N 22/00
[52] U.S. Cl. ....................................... 324/639; 73/23; 324/636
[58] Field of Search ................. 324/58 R, 58 A, 58 C, 324/58.5 R, 58.5 A, 58.5 C; 73/23, 1 R

[56] References Cited

U.S. PATENT DOCUMENTS

| | | | |
|---|---|---|---|
| 2,982,855 | 5/1961 | Wickersham | 324/58.5 A |
| 3,443,217 | 5/1969 | Brinkerhoff | 324/58.5 A |
| 3,973,186 | 8/1976 | Uehara et al. | 324/58.5 A |

Primary Examiner—Reinhard J. Eisenzopf
Assistant Examiner—Robert W. Mueller
Attorney, Agent, or Firm—Spencer & Frank

[57] ABSTRACT

A method for analyzing a gaseous medium with respect to a component having a characteristic absorption frequency spectral line, including the steps of generating microwave radiation at a selected frequency, generating a first Stark voltage selected to have a value such that a reference signal produced by subjecting the component to the microwave radiation and the first Stark voltage has a zero passage, resulting from the change in polarity between the spectral line and the Stark voltage lines, at a frequency coinciding with the characteristic absorption frequency spectral line, and regulating the microwave radiation frequency as a function of frequency shifts of the zero passage of the reference signal.

24 Claims, 7 Drawing Sheets

METHOD AND APPARATUS FOR ANALYSIS OF GAS BY MEANS OF ABSORPTION FREQUENCY REGULATION

BACKGROUND OF THE INVENTION

The present invention relates to a method for the analysis, in particular, of gaseous media by means of microwave absorption, with microwave radiation of at least one frequency being generated, and to an apparatus for the analysis of gaseous media based on the absorption of microwaves, particularly with the use of the Stark effect, primarily for implementing the method, the apparatus including at least one microwave transmitter, at least one measuring cell, at least one detector, amplifying and display devices for the measurement signal, a regulating device for the microwave transmitter and a Stark generator.

It is known to analyze gaseous media, possibly also after conversion of a solid substance or a liquid into the gaseous state, by absorption of microwaves within certain characteristic frequency ranges by the excitation of rotational transitions in molecules of the media to be examined.

In order to reduce the frequency line width, the examination takes place in the low pressure range. The absorption lines are split by means of the Stark effect, an alternating Stark voltage preferably being applied to increase detection sensitivity. Such a process is basically highly selective and does not require preparatory operations, such as ionization or chemical reactions, on the substances to be examined.

In the past, the examination method could practically be used only in a laboratory setting. Industrially usable apparatus was not available since the prior art apparatus was expensive because of its structural, mechanical and electrical configuration, often included sensitive components and it was a problem or involved high expenditures to stay within critical parameters.

For example, it is necessary to stabilize the frequency of the transmitted microwave, and thus to regulate in the actual sense its frequency to the absorption maximum of the molecule of interest, possibly under consideration of the Stark voltage that is acting on it. For this purpose, it has been proposed to feed part of the high frequency of the microwave radiation, supplied with the aid of a directional coupler, to a mixer diode, to there compare it with the harmonic of a stable low frequency transmitter as generated, for example, by a quartz crystal, to bind the microwave frequency to the harmonic of the lower frequency by synchronization with a PLL circuit and to thus stabilize the high frequency of the microwave on the absorption line of the component to be measured.

It has also been proposed to additionally modulate the frequency of the microwave transmitter, to transmit part of the microwave radiation through a reference cell containing the component to be measured, with the splitting of the microwave radiation again requiring the use of a directional coupler. The microwave transmitter is then fixed to the absorption line of the component to be measured with the aid of the derived signal at a reference cell detector required in addition to the detector of the measuring cell.

The drawback of such a transmitter modulation is the certainly occurring increase in noise at the detector. Particularly because of the requirement for such complicated frequency stabilization, prior art methods and apparatus were too expensive so that competing measuring methods and apparatus were more economical. As a whole, the prior art methods and apparatus were unsuitable particularly for process measuring techniques.

SUMMARY OF THE INVENTION

It is therefore an object of the present invention to provide a method and apparatus of this type which avoids the above-stated drawbacks and permits economical regulation of the microwave transmitter and, in particular, provides the prerequisites for an industrially usable microwave process analyzer. Preferably, the method operates with a single frequency.

The above and other objects are achieved, according to the invention, by a method for analyzing a gaseous medium with respect to a component having a characteristic absorption frequency spectral line, comprising: generating microwave radiation at a selected frequency; generating a first Stark voltage selected to have a value such that a reference signal produced by subjecting the component to the microwave radiation and the first Stark voltage has a zero passage, resulting from the change in polarity between the spectral line and the Stark voltage lines, at a frequency coinciding with the characteristic absorption frequency spectral line; and regulating the microwave radiation frequency as a function of frequency shifts of the zero passage of the reference signal.

The apparatus according to the invention has such a configuration that at least one reference cell is provided which is charged with a Stark voltage signal tuned in such a manner that the frequency of the zero passage of the reference cell signal caused by the change in polarity between the unshifted absorption line and the Stark lines coincides with the frequency of maximum absorption of the gaseous medium component to be examined in the measuring cell and the regulating device regulates the frequency of the microwave transmitter on the basis of deviations of the reference signal from the zero passage.

Thus frequency regulation or stabilization is effected by means of a reference cell and a smaller, tuned Stark voltage, without the high frequency transmitter having to be frequency modulated. This results in a better signal to noise ratio. A frequency normal and a mixer diode may be omitted, thus making the entire process simpler and less expensive.

In particular, it is provided to generate a first and second alternating Stark voltage with a phase shift, with preferably the Stark modulation in the measuring and reference cells occurring with a mutual phase shift of 90°. This makes it possible to provide only one detector for the reference signal as well as the measuring signal and to further provide that reference and measuring signals are detected and preamplified together, although shifted in phase, with particularly the preamplification being effected by a subcritically attenuated passive narrowband network. The phase shift between the Stark voltages for the reference cell and for the measuring cell further makes it possible that at least one reference cell and one measuring cell are placed one behind the other, that a common detector is provided for both cells and that a phase shifter is provided to generate a phase difference between the voltages for the measuring cell and the reference cell so that with such a configuration, directional couplers and harmonic mixers are no longer required.

As a whole, the configuration according to the invention results in process and structural advantages due to higher sensitivity, the elimination of highly stable low frequency transmitters and a simple regulation, with, furthermore, additional noise due to frequency modulation, as it exists in one prior art method, being avoided. The method according to the present invention ensures extremely fast response times.

Preferably it is provided that operation takes place in the power saturation range, with a lock-in amplification providing phase and frequency selective gain. With a phase optimized setting, this permits the output of the average of the rectified signal voltage as the measurement signal. In particular, if the system is limited to one measuring frequency, the electronic structure becomes compact and economical and utilizes available components. A maximum of user friendliness results with, in particular, a computer being addressable directly.

If a plurality of absorption frequencies are to be examined, it may be provided that a plurality of microwave transmitters at different frequencies are associated with one measuring cell in which case exchange of the pure gas generator, for example a permeation system, in the reference cell is avoided in that, according to a further feature, a plurality of reference cells are associated with one measuring cell, with either the reference cells being connected in parallel or in series with one another. With such multicomponent systems the microwave transmitters which preferably include Gunn oscillators, must be connected via appropriate waveguide switches, either directly with the first reference cell or, via reference cells arranged in parallel, with the common measuring cell. The significant factor is that otherwise the entire arrangement remains the same, particularly also the electronic evaluation system including primarily a detector and a preamplifier and, together with the transmitters, only the Stark voltages in the measuring and reference cells need be switched.

The measurements of the various components are effected by actuation of the respective transmitter and by applying the respective Stark voltages which, however, involves switching delays. Particularly for measurements of two components, two transmitters are thus preferred which may be connected with the measuring cell by way of switches, while the reference cells are connected in series with one another but in parallel with the measuring cell, and the reference cells are charged with phase shifted Stark voltages. In contrast to the preceding solution, a permanent frequency frequency lock is possible which avoids time delays due to renewed frequency synchronization each time.

Since it has been found that the above-mentioned zero passage of the microwave absorption signal is a function of pressure, pressure regulation is provided particularly for the reference measurement. A method according to the invention for pressure regulation is characterized in that the pressure is measured and the temperature of a permeation system for the pure gas component is regulated by means of the pressure signal. The system according to the invention is particularly advantageous because, with subatmospheric pressure on both sides, a conventional pressure regulation by way of electrical regulating valves or the like is impossible.

The pressure regulation method according to the invention is simple since the pressure is regulated with the aid of defined evaporation of the pure component to be measured. If the pressure drops due to fluctuations during extraction, i.e. by means of a pump, more intensive heating of the pure component causes it to evaporate more so that the pressure is increased; if the pressure rises, the temperature is reduced again or the system is cooled so that the amount of evaporation is reduced and the overall pressure in the cell is reduced.

Preferably, the gas is extracted from the cell at a constant rate. With a constantly operating extraction pump, a constant flow is realized in that a capillary is disposed in the extraction path. It may also be provided that filters are connected downstream of the outlet and of the reference cell. Such a filter absorbs the component to be measured and prevents, in a vacuum system, the pure component from entering into the measuring cell to there possibly falsify the measuring result.

According to a preferred embodiment, the reference cell and measuring cell have a common thermostat system. This eliminates the requirement for thermal insulation between reference cell and measuring cell.

Mechanical or electrical valves are used to regulate the pressure in the measuring cell. These valves are configured, in particular, as cross valves in which the gas fed to the measuring cell is branched off in an ancillary current from the gas flowing past an inlet opening leading to the measuring cell. This substantially reduces dead volumes which could produce the so-called memory effect. A memory effect is understood to be the fact that the measuring device emits a signal at a later time for a gas it measured some time ago.

Further advantages and features of the invention result from the description that follows in which significant features of the invention are described in detail with reference to the drawing figures.

DESCRIPTION OF THE PREFERRED EMBODIMENTS

Figure 1:
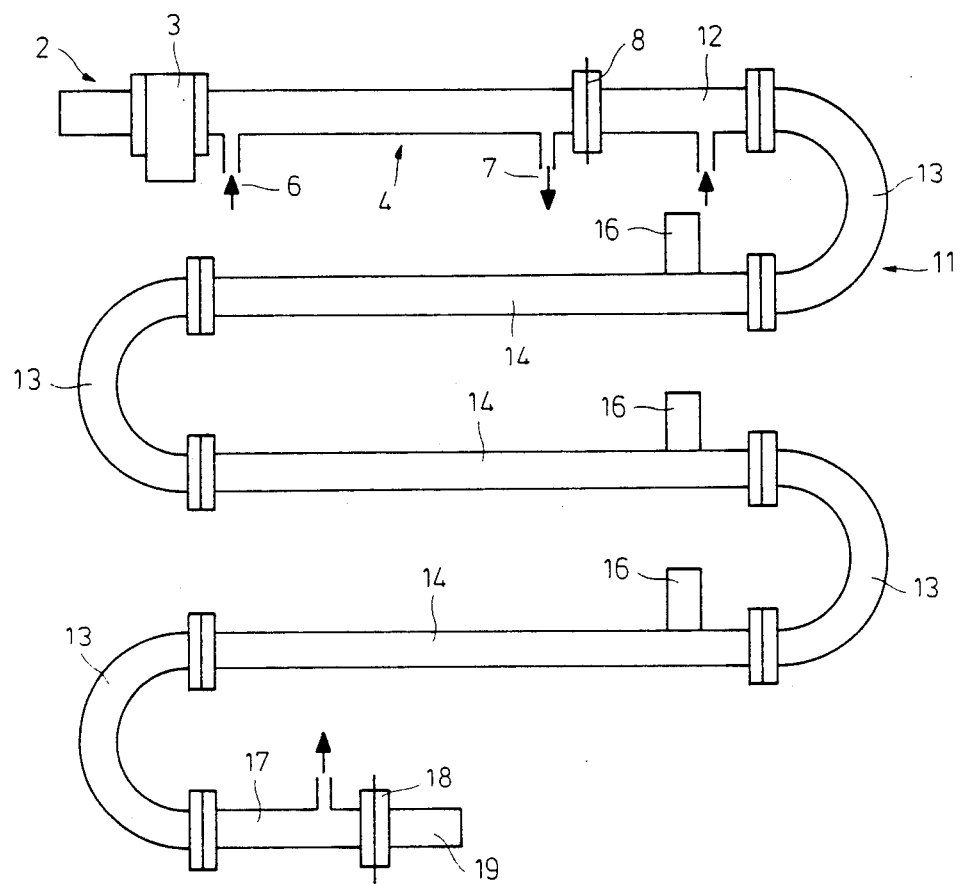
FIG. 1 is a pictorial view showing the layout of apparatus according to the invention.

FIG. 1 shows the basic overall physical arrangement of apparatus according to the invention or, more specifically, of a microwave process analyzer according to the invention.

This apparatus includes a microwave radiation transmitter 2, an isolator 3 disposed downstream thereof, and a reference cell 4 having a reference gas inlet 6 and an outlet 7. Reference cell 4 is followed by an insulating window 8, which is, in turn, followed by a measuring cell 11 having a gas inlet 12 in the region adjacent window 8. In order to avoid long structural lengths, measuring cell 11 is given a meander shape and is subdivided into a plurality of 180° arcs 13 and linear Stark chambers 14. In a conventional manner, Stark chambers 14 are provided with insulated Stark voltage leads 16.

Finally measuring cell 11 has a gas outlet 17 followed by a detector 19 separated from cell 11 by a further insulating window 18.

Cells 4 and 11 constitute a waveguide and the cross section of measuring cell 11 and, in particular, of Stark chambers 14 is optimized for the respective microwave range in which the apparatus is to operate. In particular, if only one frequency is to be analyzed, the cross section is tuned to that frequency. The cross section is preferably 7.1 mm×3.6 mm.

Preferably, microwave transmitter 2 includes a Gunn oscillator. If a plurality of gas components are to be analyzed, a plurality of transmitters may be connected, each via an appropriate waveguide switch, to common measuring/reference cells, with possibly one cell containing the components to be examined. The Stark voltages in the measuring and reference cell, respectively, are switched in to correspond to the active transmitters. In the case of a multicomponent gas system it may also be provided that, if the respective component is available for the reference cell in its pure form, a plurality of reference cells are connected mutually in parallel or all in series downstream of their associated transmitters and are switched in according to the respective measurement to be performed.

Stark chamber 14 and a septum held therein in an insulated manner create the required Stark capacitance. The Stark voltage supply 16 has such a configuration that it has an external inductance which forms with the capacitance of Stark electrode a parallel resonant circuit, with such external inductance, in turn, simultaneously serving as the high voltage coil of a transformer.

At the same time, the series connection of a capacitance, which has a much greater value than the capacitance of the Stark cells, in the resonant circuit and the incorporation of a diode with series resistance parallel to the Stark capacitance raises the d.c. level of the alternating Stark voltage in such a manner that the negative peak value of the alternating voltage is positioned at 0 volt.

Figure 2:
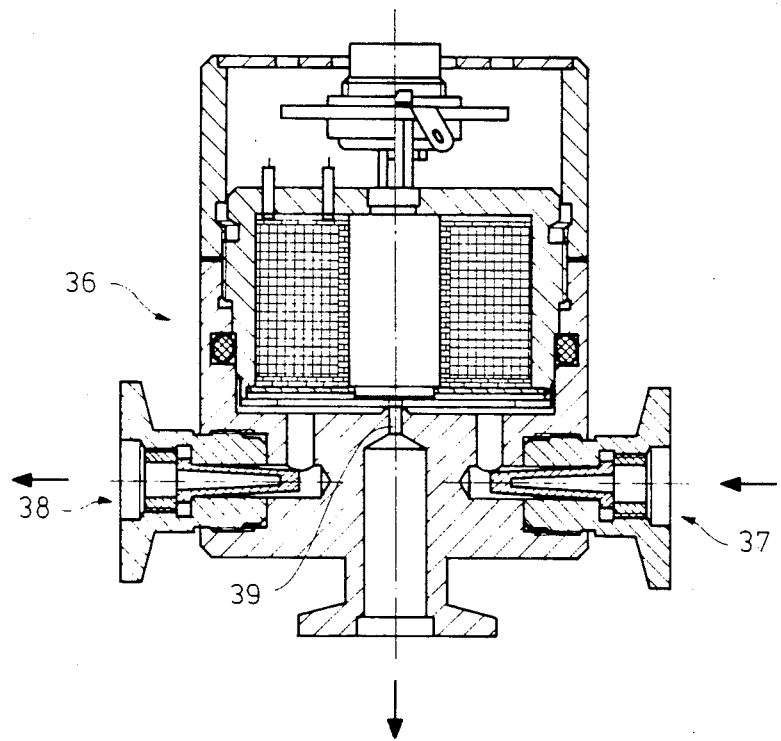
FIG. 2 is a cross-sectional view of a valve arrangement for supplying measuring gas to a measuring cell.

The inlet 12 is further connected with a so-called cross valve 36 as shown in FIG. 2. In the valve, the gas to be supplied to the respective measuring chamber 14 is branched off via a side branch 39 by a valve which, when open, leads from its inlet 37 to the valve outlet 38. This reduces the amount of dead volume, because the sample to be analyzed is brought directly to the boundary between high pressure system 37/38 and the vacuum system 39.

Figure 3:
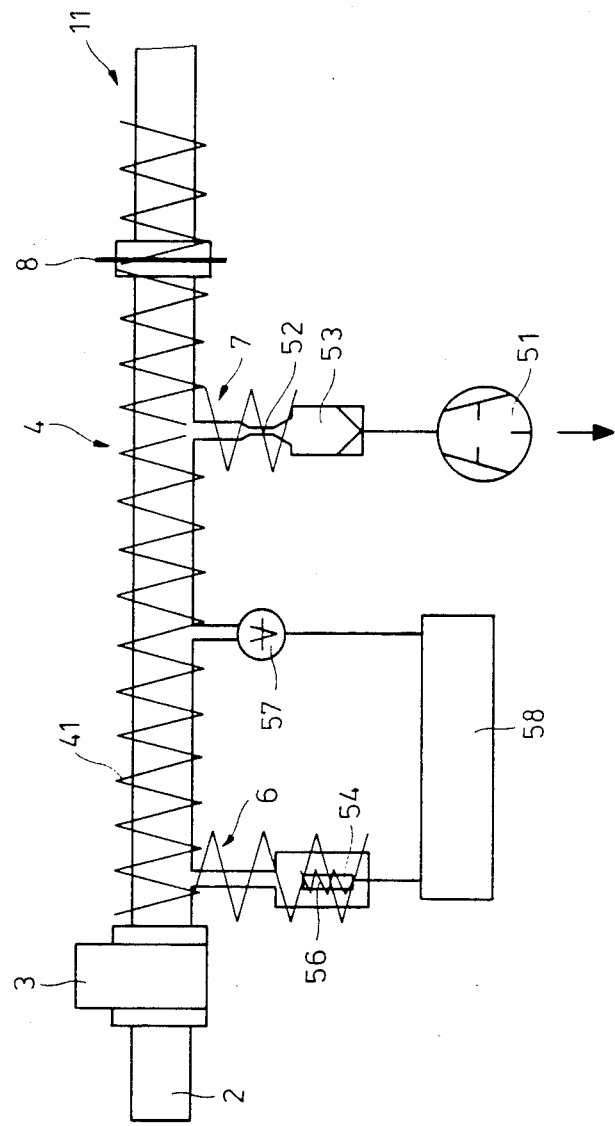
FIG. 3 is a simplified pictorial illustration of a pressure and temperature regulation arrangement.

FIG. 3 shows that reference cell 4 and measuring cell 11 are kept at the same temperature by a joint thermostat system 41. In this way, thermal insulation between the two systems is no longer necessary.

A constant pressure must be maintained particularly in the reference cell 4. For that reason, the pressure regulation effected in measuring cell 11 by way of a regulating valve following up is not sufficient if there are fluctuations in the pump output of the vacuum system.

Initially a conventional vacuum pump 51 is connected to outlet 7 of reference cell 14. Outlet 7 has a capillary 52 which produces a constant gas flow. If only one vacuum system is employed, a filter 53 is connected downstream of capillary 52 to absorb the component to be measured and to thus prevent this component from reaching the measuring cell as a pure substance which would falsify the measurement. The samples to be analyzed flow from inlet 37 to the outlet 38 of the valve passing the boundary to the vacuum system. A small amount of gas is pumped through 39 into the measuring cell.

The pure substance required for the reference cell 4 is made available in a permeation vessel 54 containing it. Commerically made permeation tubes are attached to a Peltier element and placed into the vacuum chamber.

This vessel is provided with a separate heating and/or cooling system 56 controlled in the following manner by means of a pressure regulating device 58 which is connected with a pressure sensor 57: if the suction output of the vacuum system 51 fluctuates, pressure fluctuations may occur in spite of the effect of capillary 52. These fluctuations are measured by pressure sensor 57 which, via pressure regulator 58 of permeation vessel 54, if the pressure drops, heats vessel 54 to increase permeation of the pure component and if the pressure increases, reduces the heating or cools vessel 54 to thus reduce the permeation output. This results in a precise and reliable pressure regulation.

A relatively good pressure constant is particularly necessary to regulate the microwave frequency and thus to stabilize it.

Figure 4:
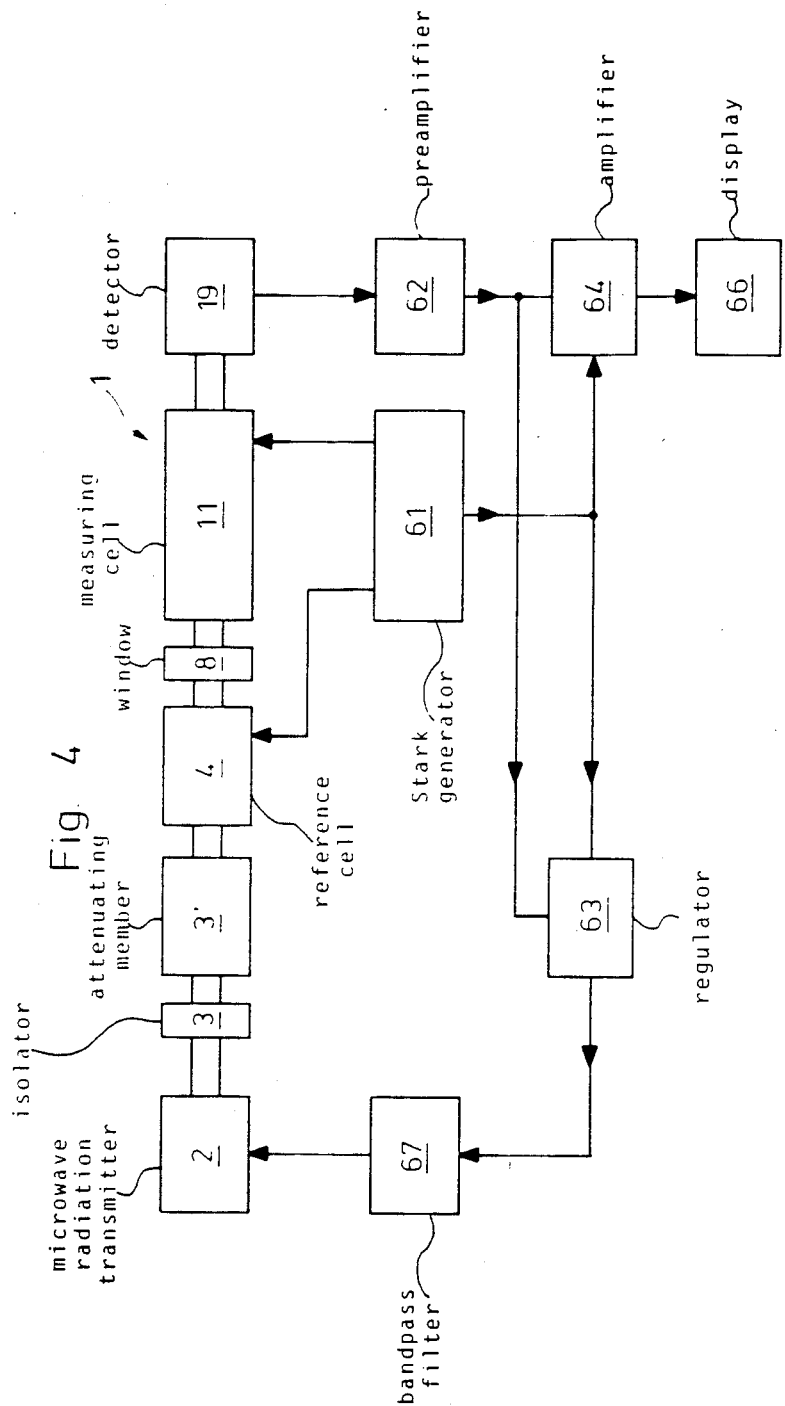
FIG. 4 is a block circuit diagram of a system according to the invention.

This will be described below with reference to FIGS. 4 and 5. In this connection, FIG. 4 is a block circuit diagram of the entire apparatus according to the invention including its electronic components. The same parts bear the same reference numerals as in FIG. 1. Isolator 3 has an associated attenuating member 3'. FIG. 4 shows a Stark generator 61 for generating Stark voltages in reference cell 4 and measuring cell 11.

Detector 19 has an associated preamplifier 62 whose output is connected, on the one hand, with a regulating unit 63, e.g., a lock-in amplifier for microwave transmitter 2 and, on the other hand, via a lock-in amplifier 64, with a display 66 for the measurement signal. A band-pass filter 67 is connected between the output of the regulating unit 63 and the input of microwave transmitter 2. The preamplifier 62 is preferably configured as a subcritical attenuated, passive highpass network having a bandpass characteristic at the resonant frequency.

Regulation, and thus stabilization, of the frequency of microwave transmitter 2 and of its Gunn oscillator is effected in the following manner: A further Stark voltage shifted in phase with respect to the frequency modulated Stark voltage supplied to measuring cell 11, preferably by 90°, is derived from Stark oscillator 61 and fed to reference cell 4.

The Stark voltages are both sinoidal, one phase of the sine wave clamped to zero, with a modulation frequency of 50 kHz, but a phase difference of 90° to each other. The peak amplitude is 290 volts for the measuring cell and 60 volts for the reference cell.

Figure 5:
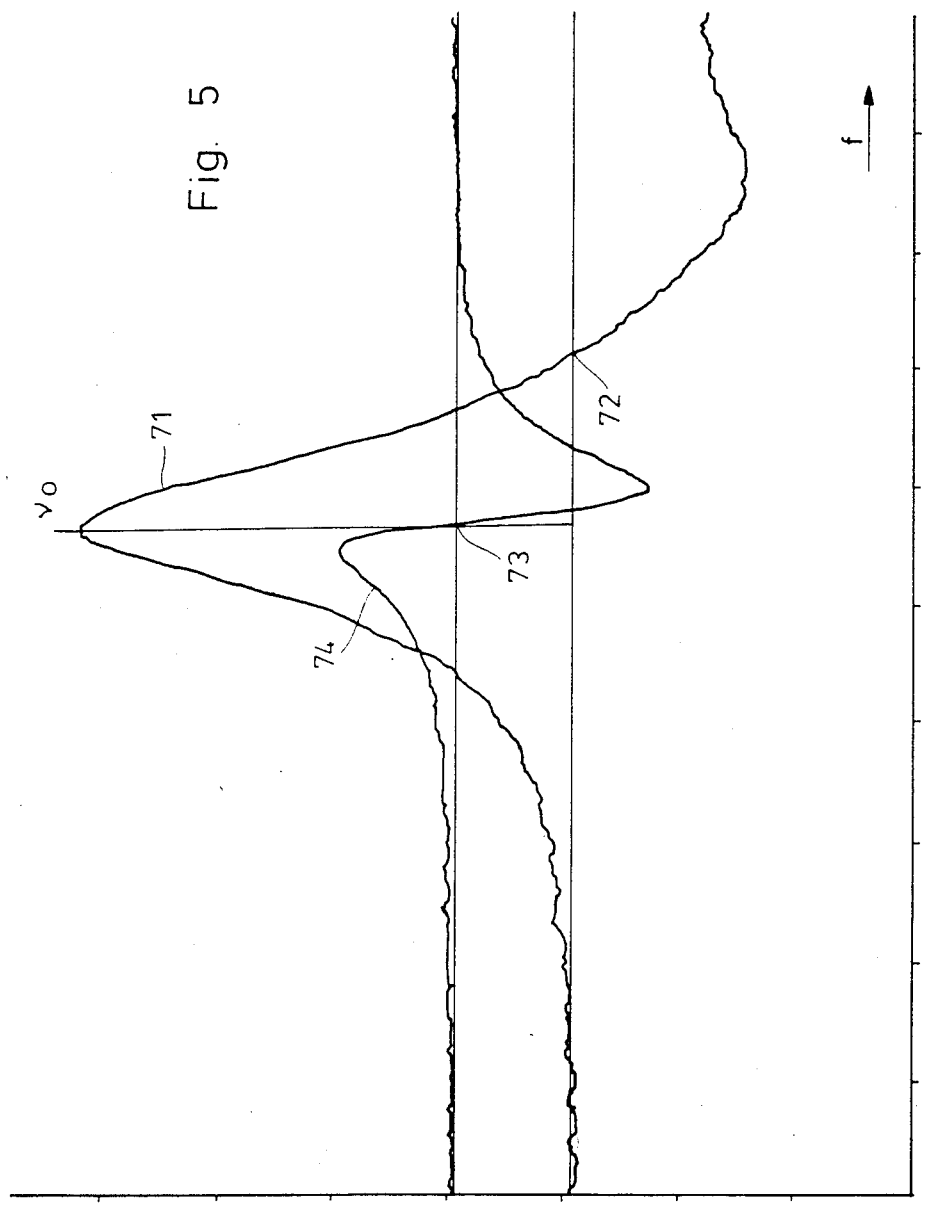
FIG. 5 is a waveform diagram illustrating microwave frequency regulation according to the invention.

In FIG. 5, signal intensities are plotted as a function of frequency, with the rotational transition modulated out by means of the Stark voltage. The illustration indicates that a zero passage exists at 72 for the spectrum 71 which results from the phase difference of 180° between the signal of the unshifted (and unsplit) rotational transition at frequency $V_o = 28.97$ GHz and the signal of the Stark components split and shifted to higher frequencies by the electric field. The respective zero passage 73 is utilized in reference cell 4 for purpose of regulation and stabilization. Reference cell 4 is charged with a Stark voltage amplitude selected in such a manner that the zero passage 73 of reference signal 74 (for the sake of clarity, measuring signal 71 and reference signal 74 are shown vertically shifted in FIG. 5) is at a frequency which just coincides with the unshifted absorption frequency Vo of measurement signal 71. Zero passage 73 is selected because its position, in view of the steep slope of reference signal 74, can be better detected in its range than the maximum of signal 74. After this calibration, the zero passage in the actual measurement results from the change in polarity during processing of the measured reference signal.

FIG. 5 shows the spectra of formaldehyde as a function of frequency (x-axis): spectrum 71 in the measuring cell with a maximum of absorption at frequency $V_o=28.97$ GHz and spectrum 74 in the reference cell with the zero paassage 73 at frequency $V_o$. Modulation frequency of the Stark voltage in each cell is 50 kHz, but with a difference in phase to each other of 90°. The peak amplitude of the Stark voltages are: In the measuring cell 290 volts and in the reference cell 60 volts, this leads to Stark field strength of $E=800$ V/cm in the measuring cell and $E=160$ V/cm in the reference cell. Pressure in the measuring cell is 0.05 mbar with a concentration of 2‰ $CH_2O$ in $N_2$, while the pressure in the reference cell is 0.03 mbar containing a pure sample of formaldehyde. Spectra are taken at room temperature.

If now, after the above described tuning, fluctuations occur in the microwave frequency with respect to the absorption frequency Vo during the taking of the actual measurements, the result will be that detector 19 no longer measures the zero passage 73 of reference signal 74 but is charged with a finite, positive or negative, voltage of the reference signal which is then utilized to regulate microwave transmitter 2.

As the lock-in amplifiers 63 and 64 are phase selective, the signals of measuring cell and reference cell can be distinguished, because their phase difference is 90° to each other. The Stark generator 61 gives the appropriate phase information to 63 and 64 respectively.

The reference circuit as well as the measuring branch include a known frequency selective, lock-in amplifiers. The latter produces practically a keyed rectification upon reversal of polarity, with the control signal possibly being derived from the oscillator for the alternating Stark voltage.

The amplifier is phase selective. Measuring and reference signals shifted in phase by 90° with respect to one another can be separated, by means of suitable phase positions of the sampling moments, into the measuring and reference branches of the circuit. This is done in that, of the signal picked up by the detector, which contains reference and measurement components, only the in-phase component which is in phase with the control voltage is rectified in each branch while the component shifted in phase by 90° is lifted out.

Phase shifts in the measurement and reference signals from the detector reaching the lock-in amplifier with respect to the alternating Stark voltages due to electronic components can be considered with the aid of a digital phase shifter. For this purpose, an oscillator signal, from which, for example, the frequency of the Stark voltage has been derived by division is fed to a counter which is set by a set signal, for example the signal on which the alternating Stark voltage is based, to the respectively preselected binary value. Output pulses are generated in time corresponding to the binary value after setting and these are converted in a known manner to a symmetrical wave now shifted in phase by the desired amount at the frequency of the set signal. This wave then forms the above-mentioned control signal.

With, for example, an output frequency of 10 MHz from a quartz oscillator and fixed division by 200, a phase shift can be made, for example in 200 steps of 1.8° each. The phase shift can be switched on once and is automatically reproducible even if the device is turned on again. It may be actuated directly by a computer. A frequency determining bias can be derived from the reference signal of the reference cell and fed to the oscillator. If, due to the microwave frequency running out of the absorption frequency and thus out of the zero passage of the reference cell signal, a finite voltage is generated in the reference branch, regulator 63 provides the appropriate correction voltage.

The measuring signal can be displayed or utilized further to control processes.

The actual intensity measurement is made at the maximum of the absorption line and, in order to prevent the influence of power fluctuations, work takes place in the power saturation range. This method ensures rapid response times for the measuring system, but requires correspondingly high power microwave transmitters having an output of 20 to 60 mW.

Figure 6:
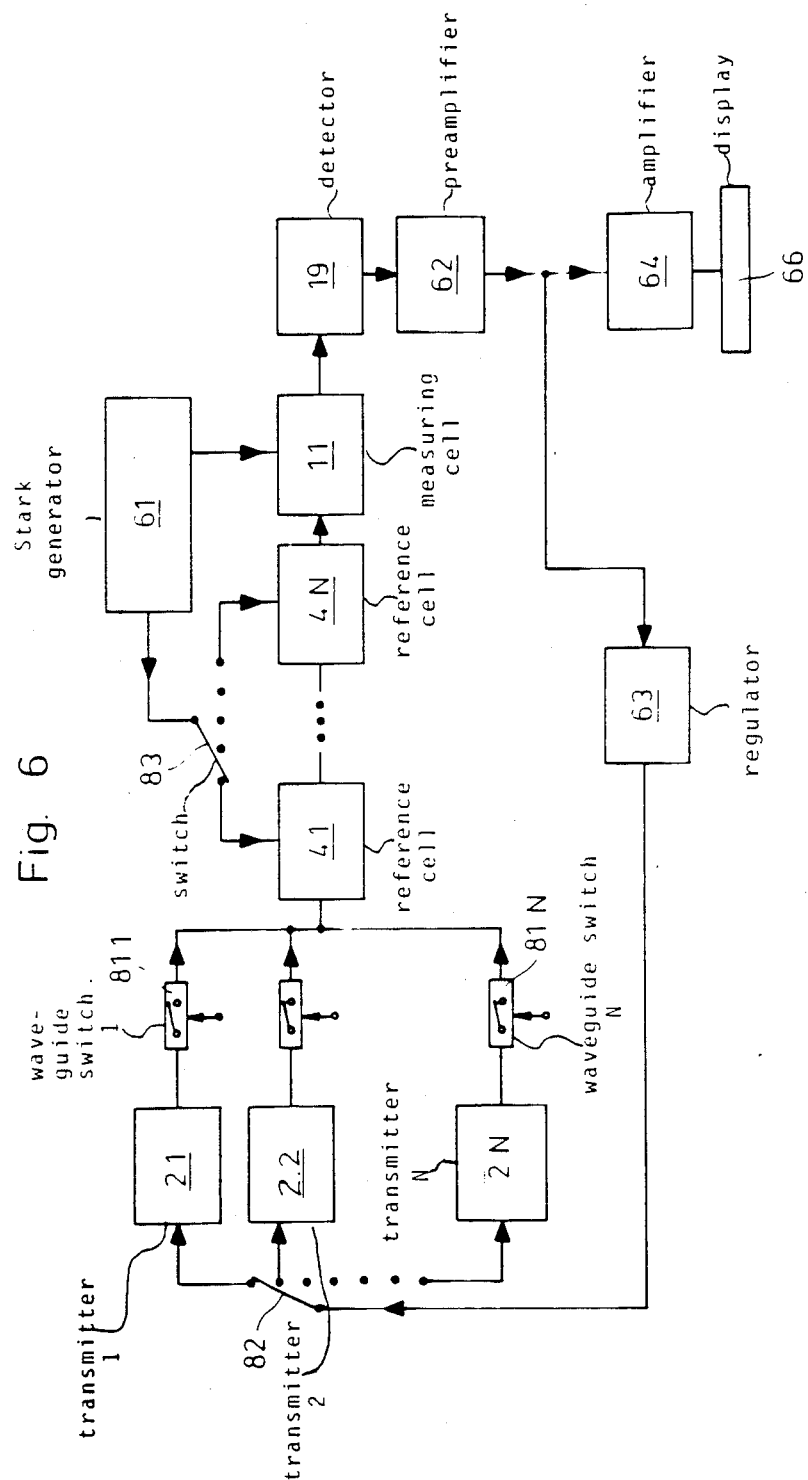
FIG. 6 is a diagram similar to that of FIG. 4 of a preferred embodiment of a multicomponent system.

FIG. 6 shows, as a comparison to FIG. 1, a first multicomponent gas measuring system having a plurality of reference cells 4.1 to 4.N connected one below the other, e.g. in a serpentine arrangement, and in series with measuring cell 11. Reference cells 4.1 to 4.N are connected via respective waveguide switches 81.1 to 81.N with tuned transmitters 2.1 to 2.N. A selected transmitter can be actuated by operating power supplied via a switch 82, while Stark voltages are applied from a Stark voltage generator 61 via a switch 83 to the respective reference cell 4.1 to 4.N.

The measurement is made in such a manner that initially the correspondingly preset Stark voltage is applied via switch 83 to reference cell 4.1 and switch 82 is used to actuate transmitter 2.1 which is then connected via waveguide switch 81.1 with the waveguide system, then a measurement is made and measurements of the gas components contained in the further reference cells are made successively thereafter.

Figure 7:
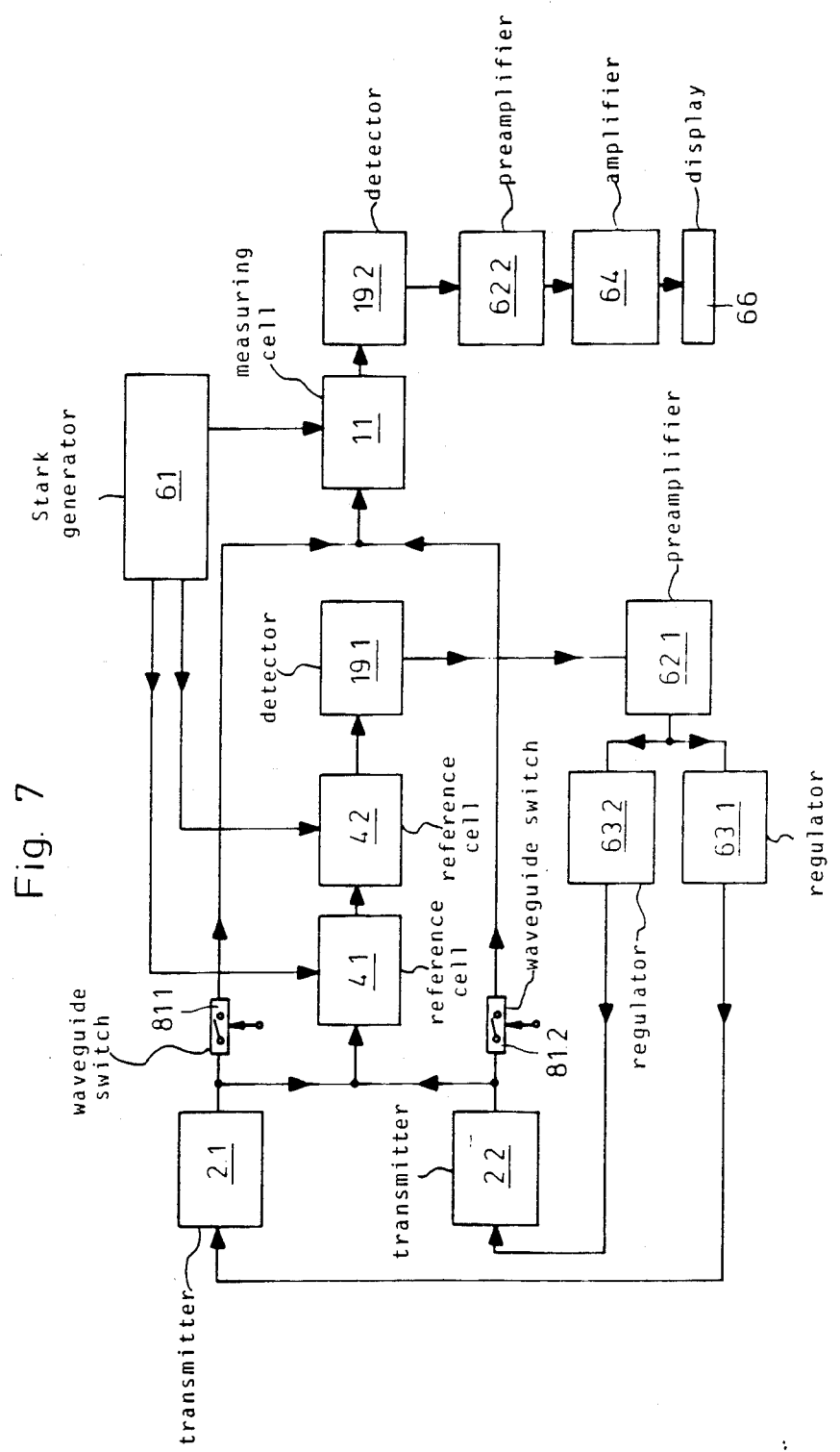
FIG. 7 is a diagram similar to that of FIG. 6 of a different type of two-component system.

The delay required in the above described embodiment to achieve the frequency synchronization of the transmitters which is necessary after each switching process can be avoided in the embodiment according to FIG. 7. Here two transmitters 2.1 and 2.2 are connected with series connected reference cells 4.1 to 4.2 which are supplied with mutually phase shifted alternating Stark voltages from generator 61. Each transmitter can additionally be selectively connected via a receptive waveguide switch 81.1 or 81.2 to measuring cell 11, which must not be overloaded by connecting both transmitters to it at the same time. The frequencies of transmitters 2.1 and 2.2 are regulated by regulators 63.1 and 63.2 respectively, which are each connected to the output of a detector 19.1 for the reference cells via a preamplifier 62.1. Both transmitters here operate continuously and are also tuned continuously so that the suitable microwave frequency is immediately available at measuring cell 11 as soon as switch 81.1 or 81.2 is thrown. A second detector 19.2 has an associated preamplifier 62.2 which is connected via lock-in amplifier 64 with display 66 for the measurement signal.

The reference cell need not in every case itself contain the pure component to be examined. If highly toxic or explosive substances are being measured, another chemical compound can also be used in its place. Such a reference compound is then selected according to the criterion that it must have an absorption line in the immediate vicinity of the selected rotational transition of the to be measured component.

By applying a direct voltage or voltages, and superposing it with the alternating Stark voltage in a reference and/or measuring cell, the S-shaped curve of the reference cell and the absorption line can be shifted with respect to one another in such a manner that the zero passage again takes place at the frequency of the line maximum.

Example: measurement of chlorine cyanide at V=35,825.95 MHz.

The two closest absorption lines of other compounds are:

toward lower frequencies $CH_3SiHDF$, V=35,825.5 Mhz;

toward higher frequencies $CHD_2NC$, V=35,827.44 MHz.

The simultaneous presence of the measuring component ClCN and methyl deutero fluorosilane or dideutero methyl isocyanide in the measuring gas can be excluded and thus V(ClCN)=35,825.95 MHz is suitable for a quantitative determination. On the other side, the absorption lines of the partially deuterized compounds lie so closely together that the application of slight direct voltages already produces a suitable curve shape.

The invention now being fully described, it will be apparent to one of ordinary skill in the art that many changes and modifications can be made thereto without departing from the spirit or scope of the invention as set forth herein.

The present disclosure relates to the subject matter disclosed in German Appllications P 36 22 957.1 and P 36 22 956.3 of July 9th, 1986, the entire specifications of which are incorporated herein by reference.

What is claimed:

1. A method for analyzing a gaseous medium with respect to a component having a characteristic absorption frequency spectral line, comprising: generating microwave radiation at a selected frequency; generating a first Stark voltage selected to have a value such that a reference signal produced by subjecting the component to the microwave radiation and the first Stark voltage has a zero passage, resulting from the change in polarity between the spectral line and the Stark voltage lines, at a frequency coinciding with the characteristic absorption frequency spectral line; and regulating the microwave radiation frequency as a function of frequency shifts of the zero passage of the reference signal.

2. A method as defined in claim 1 further comprising generating a second Stark voltage, subjecting the gaseous medium to the microwave radiation and the second Stark voltage, and measuring the passage of radiation through the medium to produce a measurement signal.

3. Method as defined in claim 2, wherein, upon the beginning of the Stark effect on the measurement signal, the first and second Stark voltages are modulated with a shift in phase.

4. Method as defined in claim 3 wherein the modulation is effected with a phase shift of 90°.

5. Method as defined in claim 2 wherein the second Stark voltage is supplemented by an inductance supplementing the Stark capacitance directly to form a parallel resonant circuit and constituting the high voltage coil of a transformer.

6. Method as defined in claim 2 wherein the reference signal and the measurement signal are subjected to a common, though phase shifted, detection and preamplification.

7. Method as defined in claim 6 wherein the preamplification is effected by means of a subcritical, attenuated, passive LC highpass network, with the bandpass character being utilized at the resonant frequency.

8. Method as defined in claim 2 wherein a lock-in amplification produces aa phase and frequency selected gain of the signals.

9. Method as defined in claim 2 further comprising extracting gas from a microwave absorption reference cell in which the first Stark voltage is generated so as to create a subatmospheric pressure and regulating the temperature of a permeation system for the component in pure form in such a manner that the pressure in the reference cell remains constant.

10. Method as defined in claim 9 wherein the gas is extracted from the reference cell at a constant rate.

11. Apparatus for the analysis of gaseous media by absorption of microwave radiation, comprising: at least one measuring cell; at least one reference cell; at least one microwave radiation transmitter disposed for directing microwave radiation into said cells; measuring means including a detector and amplifying and display devices for sensing radiation propagated through each said cell and for producing a reference signal dependent on microwave radiation propagated through said reference cell; a Stark voltage generator; means associated with said reference cell for generating therein a Stark voltage signal which is tuned to a value such that the reference signal produced by subjecting a selected gaseous medium component having a characteristic absorption frequency spectral line to the microwave radiation and the Stark voltage in said reference cell has a zero passage, resulting from the change in polarity between the spectral line and the Stark voltage lines, at a frequency coinciding with the characteristic absorption frequency spectral line; and regulating means connected to said transmitter for regulating the microwave radiation frequency as a function of frequency shifts of the zero passage of the reference signal.

12. Apparatus as defined in claim 11 wherein: there is one reference cell and one measuring cell; said cells are connected together to form a series path for propagating the microwave radiation; said measuring means are composed of a single detector associated with both of said cells; and said apparatus further comprises means associated with said measuring cell for generating therein a Stark voltage, and a phase shifter connected for establishing a phase difference between the Stark voltage in said reference cell and the Stark voltage in said measuring cell.

13. Apparatus as defined in claim 12 wherein said measuring means comprise a single preamplifier associated with both of said cells.

14. Apparatus as defined in claim 13, wherein the preamplifier is configured as a subcritical, attenuated, passive highpass network having bandpass characteristic at the resonant frequency.

15. Apparatus as defined in claim 11 wherein said measuring means comprise a phase selective bandpass filter.

16. Apparatus as defined in claim 11 wherein there are a plurality of microwave radiation transmitters operating at respectively different frequencies and all arranged for directing microwave radiation into said measuring cell.

17. Apparatus as defined in claim 16 wherein there are a plurality of reference cells and one measuring cell.

18. Apparatus as defined in claim 17 wherein the reference cells are connected in series with respect to microwave radiation.

19. Apparatus as defined in claim 17 wherein the reference cells are connected in parallel with the measuring cell.

20. Apparatus as defined in claim 11 wherein said microwave transmitter comprises a Gunn oscillator.

21. Apparatus as defined in claim 11 further comprising: a permeation system connected for supplying the component in pure form to said reference cell, said permeation system including a source of the component, a temperature of regulating device for regulating the temperature of said source, and a pressure regulating device connected for controlling said temperature regulating device; and a pressure sensor connected for sensing the gas pressure in said reference cell and for controlling said pressure regulating device.

22. Apparatus as defined in claim 21 wherein said reference cell has a gas outlet, and further comprising a capillary member connected downstream of said outlet for effecting flow stabilization.

23. Apparatus as defined in claim 21 wherein said reference cell has a gas outlet, and further comprising gas filter means connected downstream of said outlet.

24. Apparatus as defined in claim 21 further comprising a common thermostat system for said measuring and reference cells.

* * * * *